(12) United States Patent
Stein et al.

(10) Patent No.: US 9,504,584 B1
(45) Date of Patent: Nov. 29, 2016

(54) SPINAL FUSION IMPLANT AND RELATED METHODS

(71) Applicant: NuVasive, Inc., San Diego, CA (US)

(72) Inventors: Christopher Stein, Fallbrook, CA (US); Chad Grant, Escondido, CA (US); Nathan Lovell, Oceanside, CA (US); Ryan Donahoe, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/606,501

(22) Filed: Jan. 27, 2015

Related U.S. Application Data

(63) Continuation of application No. 13/361,855, filed on Jan. 30, 2012, now Pat. No. 8,940,030.

(60) Provisional application No. 61/437,006, filed on Jan. 28, 2011.

(51) Int. Cl.
   *A61F 2/44* (2006.01)
   *A61B 17/80* (2006.01)

(52) U.S. Cl.
   CPC .......... *A61F 2/4455* (2013.01); *A61F 2/442* (2013.01); *A61B 17/8033* (2013.01); *A61B 17/8042* (2013.01); *A61F 2002/4475* (2013.01); *A61F 2220/0008* (2013.01)

(58) Field of Classification Search
   CPC . A61F 2/447; A61F 2/4455; A61B 17/8033; A61B 17/8042
   See application file for complete search history.

(56) References Cited

U.S. PATENT DOCUMENTS

| | | | |
|---|---|---|---|
| 564,097 A | 7/1896 | Nerud |
| 3,016,077 A | 1/1962 | Yocum |
| 4,484,570 A | 11/1984 | Sutter |
| 4,488,543 A | 12/1984 | Tornier |
| 5,423,826 A | 6/1995 | Coates |
| 5,531,554 A | 7/1996 | Jeanson |
| 5,578,034 A | 11/1996 | Estes |
| 5,876,402 A | 3/1999 | Errico |
| 5,931,838 A | 8/1999 | Vito |
| 5,951,558 A | 9/1999 | Fiz |
| 5,954,722 A | 9/1999 | Bono |
| 5,979,907 A | 11/1999 | Udagawa |
| 6,036,693 A | 3/2000 | Yuan |
| 6,117,173 A | 9/2000 | Taddia |
| 6,235,033 B1 | 5/2001 | Brace |
| 6,241,731 B1 | 6/2001 | Fiz |
| 6,258,089 B1 | 7/2001 | Campbell |
| 6,258,092 B1 | 7/2001 | Dall |
| 6,261,291 B1 | 7/2001 | Talaber |

(Continued)

FOREIGN PATENT DOCUMENTS

| | | |
|---|---|---|
| AU | 2006252101 A1 | 1/2007 |
| AU | 2012211502 A1 | 8/2012 |

(Continued)

*Primary Examiner* — Andrew Yang
(74) *Attorney, Agent, or Firm* — Jeremy A. Smith; Bradley Arant Boult Cummings LLP

(57) ABSTRACT

The present invention relates generally to medical devices and methods for use in spinal surgery. In particular, the disclosed devices relate to a spinal fixation system and an intervertebral spinal implant assembly sized and dimensioned for the lumbar spine implantable via an anterior or anterolateral approach. The devices include an implant, bone screws, and an improved locking mechanism to prevent the back out of screws.

20 Claims, 6 Drawing Sheets

(56) References Cited

U.S. PATENT DOCUMENTS

| | | |
|---|---|---|
| 6,306,139 B1 | 10/2001 | Fuentes |
| 6,331,179 B1 | 12/2001 | Freid |
| 6,361,537 B1 | 3/2002 | Anderson |
| 6,364,880 B1 | 4/2002 | Michelson |
| 6,413,259 B1 | 7/2002 | Lyons |
| 6,485,517 B1 | 11/2002 | Michelson |
| 6,558,387 B2 | 5/2003 | Errico |
| 6,558,423 B1 | 5/2003 | Michelson |
| 6,602,255 B1 | 8/2003 | Campbell |
| 6,602,256 B1 | 8/2003 | Hayes |
| 6,602,257 B1 | 8/2003 | Thramann |
| 6,613,053 B1 | 9/2003 | Collins |
| 6,652,525 B1 | 11/2003 | Assaker |
| 6,669,700 B1 | 12/2003 | Farris |
| 6,755,833 B1 | 6/2004 | Paul |
| 6,780,186 B2 | 8/2004 | Errico |
| 6,899,735 B2 | 5/2005 | Coates |
| 6,902,567 B2 | 6/2005 | Del Medico |
| 6,926,718 B1 | 8/2005 | Michelson |
| 7,004,944 B2 | 2/2006 | Gause |
| 7,025,769 B1 | 4/2006 | Ferree |
| 7,060,067 B2 | 6/2006 | Needham |
| 7,094,239 B1 | 8/2006 | Michelson |
| 7,175,623 B2 | 2/2007 | Thramann |
| 7,220,263 B2 | 5/2007 | Cordaro |
| 7,288,094 B2 | 10/2007 | Lindemann |
| 7,303,564 B2 | 12/2007 | Freid |
| 7,309,340 B2 | 12/2007 | Fallin |
| D564,097 S | 3/2008 | Olerud |
| 7,358,005 B2 | 4/2008 | Bourgeois |
| 7,438,715 B2 | 10/2008 | Doubler |
| 7,452,370 B2 | 11/2008 | Anderson |
| 7,488,321 B2 | 2/2009 | Lin |
| 7,524,325 B2 | 4/2009 | Khalili |
| 7,575,588 B2 | 8/2009 | Barker |
| 7,591,840 B2 | 9/2009 | Suddaby |
| 7,621,957 B2 | 11/2009 | Errico |
| 7,625,375 B2 | 12/2009 | Garden |
| 7,651,517 B2 | 1/2010 | Konieczynski |
| 7,655,028 B2 | 2/2010 | Kirschman |
| 7,662,154 B2 | 2/2010 | Ribeiro |
| 7,662,174 B2 | 2/2010 | Doubler |
| 7,674,279 B2 | 3/2010 | Johnson |
| 7,691,133 B2 | 4/2010 | Partin |
| 7,699,880 B2 | 4/2010 | Orbay |
| 7,704,250 B2 | 4/2010 | Michelson |
| 7,736,380 B2 | 6/2010 | Johnston |
| 7,758,620 B2 | 7/2010 | Porcher |
| 7,785,327 B1 | 8/2010 | Navarro |
| 7,803,157 B2 | 9/2010 | Michelson |
| 7,811,285 B2 | 10/2010 | Michelson |
| 7,819,903 B2 | 10/2010 | Fraser |
| 7,833,226 B2 | 11/2010 | Grabowski |
| 7,846,163 B2 | 12/2010 | Fourcault |
| 7,846,190 B2 | 12/2010 | Ball |
| 7,867,239 B2 | 1/2011 | Muhanna |
| 7,887,547 B2 | 2/2011 | Campbell |
| 7,981,142 B2 | 7/2011 | Konieczynski |
| 7,985,224 B2 | 7/2011 | Michelson |
| 8,029,514 B2 | 10/2011 | Robinson |
| 8,048,131 B2 | 11/2011 | Dalton |
| 8,057,522 B2 | 11/2011 | Rothman |
| 8,062,367 B2 | 11/2011 | Kirschman |
| 8,066,751 B2 | 11/2011 | Podgorski |
| 8,114,139 B2 | 2/2012 | Sournac |
| 8,118,847 B2 | 2/2012 | Wallenstein |
| 8,142,477 B2 | 3/2012 | Eckhardt |
| 8,152,838 B2 | 4/2012 | Ensign |
| 8,172,885 B2 | 5/2012 | Songer |
| 8,182,518 B2 | 5/2012 | Butler |
| 8,182,539 B2 | 5/2012 | Tyber |
| 8,197,520 B2 | 6/2012 | Salemi |
| 8,211,148 B2 | 7/2012 | Zhang |
| 8,211,154 B2 | 7/2012 | Fisher |
| 8,216,285 B2 | 7/2012 | Markworth |
| 8,216,312 B2 | 7/2012 | Gray |
| 8,236,033 B2 | 8/2012 | Paul |
| 8,241,287 B2 | 8/2012 | Prager |
| 8,257,403 B2 | 9/2012 | Den Hartog |
| 8,262,666 B2 | 9/2012 | Baynham |
| 8,262,705 B2 | 9/2012 | Bray |
| 8,268,000 B2 | 9/2012 | Waugh |
| 8,282,675 B2 | 10/2012 | Maguire |
| 8,287,575 B2 | 10/2012 | Murner |
| 8,298,272 B2 | 10/2012 | Edie |
| 8,328,856 B1 | 12/2012 | Donahoe |
| 8,343,194 B2 | 1/2013 | Aflatoon |
| 8,353,939 B2 | 1/2013 | Anderson |
| 8,361,127 B2 | 1/2013 | Biedermann |
| 8,372,152 B2 | 2/2013 | Kirschman |
| 8,388,662 B2 | 3/2013 | LeHuec |
| 8,388,666 B2 | 3/2013 | Castaneda |
| 8,398,688 B2 | 3/2013 | Peukert |
| 8,403,969 B2 | 3/2013 | Wallenstein |
| 8,414,651 B2 | 4/2013 | Tyber |
| 8,425,514 B2 | 4/2013 | Anderson |
| 8,425,576 B2 | 4/2013 | Anderson |
| 8,425,607 B2 | 4/2013 | Waugh |
| 8,425,613 B2 | 4/2013 | Theofilos |
| 8,430,929 B2 | 4/2013 | Tribus |
| 8,439,977 B2 | 5/2013 | Kostuik |
| 8,454,666 B2 | 6/2013 | Tornier |
| 8,460,387 B2 | 6/2013 | Theofilos |
| 8,460,388 B2 | 6/2013 | Kirwan |
| 8,480,739 B2 | 7/2013 | Lim |
| 8,486,115 B2 | 7/2013 | Fisher |
| 8,486,120 B2 | 7/2013 | Shimko |
| 8,496,692 B2 | 7/2013 | Bhatnagar |
| 8,500,737 B2 | 8/2013 | Richelsoph |
| 8,523,947 B2 | 9/2013 | Theofilos |
| 8,540,756 B2 | 9/2013 | Olsen |
| 8,551,144 B2 | 10/2013 | Youssef |
| 8,562,655 B2 | 10/2013 | Butler |
| 8,562,656 B2 | 10/2013 | Humphreys |
| 8,574,271 B2 | 11/2013 | Crainich |
| 8,591,555 B2 | 11/2013 | Foley |
| 8,591,588 B2 | 11/2013 | Fraser |
| 8,597,353 B2 | 12/2013 | Kana |
| 8,613,761 B2 | 12/2013 | Lindemann |
| 8,617,222 B2 | 12/2013 | Shipp |
| 8,652,183 B1 | 2/2014 | Truman |
| 8,668,741 B2 | 3/2014 | Michelson |
| 8,672,984 B2 | 3/2014 | Lindemann |
| 8,696,715 B2 | 4/2014 | Sidebotham |
| 8,696,957 B2 | 4/2014 | Dougherty |
| 8,702,764 B2 | 4/2014 | Rusch |
| 8,728,130 B2 | 5/2014 | Kirschman |
| 8,753,400 B2 | 6/2014 | Ciupik |
| 8,778,001 B2 | 7/2014 | Thramann |
| 8,784,498 B2 | 7/2014 | Scheland |
| 8,795,373 B2 | 8/2014 | Jones |
| 8,795,376 B2 | 8/2014 | Lin |
| 8,814,869 B2 | 8/2014 | Freid |
| 8,821,554 B2 | 9/2014 | Stanaford |
| 8,821,555 B2 | 9/2014 | Bae |
| 8,828,064 B2 | 9/2014 | Ziolo |
| 8,828,084 B2 | 9/2014 | Aflatoon |
| 8,834,570 B2 | 9/2014 | Biedermann |
| 8,840,650 B2 | 9/2014 | Cawley |
| 8,845,737 B2 | 9/2014 | Melkent |
| 8,852,247 B2 | 10/2014 | Abdelgany |
| 8,870,932 B2 | 10/2014 | Robinson |
| 8,870,961 B2 | 10/2014 | Thalgott |
| 8,882,813 B2 | 11/2014 | Jones |
| 8,882,843 B2 | 11/2014 | Michelson |
| 8,894,712 B2 | 11/2014 | Varela |
| 8,900,277 B2 | 12/2014 | Perrow |
| 8,926,702 B2 | 1/2015 | Gorek |
| 8,932,359 B2 | 1/2015 | Brett |
| 8,945,226 B2 | 2/2015 | Johnston |
| 8,956,415 B2 | 2/2015 | Cowan |
| 8,956,416 B2 | 2/2015 | McCarthy |
| 8,961,607 B2 | 2/2015 | Bucci |
| 8,998,963 B2 | 4/2015 | Ziolo |

(56) References Cited

U.S. PATENT DOCUMENTS

| | | |
|---|---|---|
| 8,998,964 B2 | 4/2015 | Robinson |
| 8,998,988 B2 | 4/2015 | Phillips |
| 9,005,256 B2 | 4/2015 | Weiman |
| 9,005,292 B2 | 4/2015 | Melamed |
| 9,005,295 B2 | 4/2015 | Kueenzi |
| 9,005,296 B2 | 4/2015 | Zipnick |
| 2003/0105462 A1 | 6/2003 | Haider |
| 2003/0149434 A1 | 8/2003 | Paul |
| 2003/0208204 A1 | 11/2003 | Bailey |
| 2004/0204712 A1 | 10/2004 | Kolb |
| 2004/0220571 A1 | 11/2004 | Assaker |
| 2005/0021032 A1 | 1/2005 | Koo |
| 2005/0187551 A1 | 8/2005 | Orbay |
| 2006/0009770 A1 | 1/2006 | Speirs |
| 2006/0085071 A1* | 4/2006 | Lechmann et al. ........ 623/17.11 |
| 2006/0195089 A1 | 8/2006 | LeHuec |
| 2006/0221247 A1 | 10/2006 | Doyen |
| 2006/0293668 A1 | 12/2006 | May |
| 2007/0162019 A1 | 7/2007 | Burns |
| 2007/0225718 A1 | 9/2007 | Ensign |
| 2008/0021470 A1 | 1/2008 | Ross |
| 2008/0033438 A1 | 2/2008 | Frizzell |
| 2008/0097442 A1 | 4/2008 | Dixon |
| 2008/0177330 A1 | 7/2008 | Ralph |
| 2008/0234750 A1 | 9/2008 | Woods |
| 2008/0249625 A1* | 10/2008 | Waugh .............. A61F 2/4465 623/17.16 |
| 2008/0306550 A1 | 12/2008 | Matityahu |
| 2008/0312699 A1 | 12/2008 | Johnson |
| 2009/0030466 A1 | 1/2009 | Strauss |
| 2009/0080997 A1 | 3/2009 | Johnson |
| 2009/0098205 A1 | 4/2009 | Sharma |
| 2009/0182383 A1 | 7/2009 | Prybyla |
| 2009/0187218 A1 | 7/2009 | Schaffhausen |
| 2009/0192549 A1 | 7/2009 | Sanders |
| 2009/0222049 A1 | 9/2009 | Frigg |
| 2009/0270926 A1 | 10/2009 | Hawkes |
| 2009/0287257 A1 | 11/2009 | Hagen |
| 2009/0306667 A1 | 12/2009 | Lee |
| 2010/0016901 A1 | 1/2010 | Robinson |
| 2010/0049256 A1 | 2/2010 | Jeon |
| 2010/0087871 A1 | 4/2010 | Loyola |
| 2010/0191291 A1 | 7/2010 | Phan |
| 2010/0274358 A1 | 10/2010 | Mueller |
| 2010/0292696 A1 | 11/2010 | Chantelot |
| 2011/0093077 A1 | 4/2011 | Aebi |
| 2011/0106159 A1 | 5/2011 | Nazeck |
| 2011/0137344 A1 | 6/2011 | Rathbun |
| 2011/0160776 A1 | 6/2011 | Erickson |
| 2011/0166658 A1 | 7/2011 | Garber |
| 2011/0251689 A1 | 10/2011 | Seifert |
| 2011/0270311 A1 | 11/2011 | Assaker |
| 2011/0282392 A1 | 11/2011 | Murphy |
| 2011/0282394 A1 | 11/2011 | Wagner |
| 2011/0319943 A1 | 12/2011 | Donahoe |
| 2012/0065682 A1 | 3/2012 | Duong |
| 2012/0065688 A1 | 3/2012 | Nehls |
| 2012/0065734 A1 | 3/2012 | Barrett |
| 2012/0078310 A1 | 3/2012 | Bernstein |
| 2012/0109313 A1 | 5/2012 | Mathieu |
| 2012/0136392 A1 | 5/2012 | Keegan |
| 2012/0150301 A1 | 6/2012 | Gamache |
| 2012/0158069 A1 | 6/2012 | Abrahams |
| 2012/0179207 A1 | 7/2012 | Mekhail |
| 2012/0179259 A1 | 7/2012 | McDonough |
| 2012/0191196 A1 | 7/2012 | Louis |
| 2012/0197399 A1 | 8/2012 | Kirschman |
| 2012/0197401 A1 | 8/2012 | Duncan |
| 2012/0221061 A1 | 8/2012 | Peppers |
| 2012/0232663 A1 | 9/2012 | Zipnick |
| 2012/0245641 A1 | 9/2012 | Mekhail |
| 2012/0245690 A1 | 9/2012 | Cowan |
| 2012/0245693 A1 | 9/2012 | Gorek |
| 2012/0277872 A1 | 11/2012 | Kana |
| 2012/0277873 A1 | 11/2012 | Kana |
| 2012/0283782 A1 | 11/2012 | Ryan |
| 2012/0283784 A1 | 11/2012 | Suh |
| 2012/0303069 A1 | 11/2012 | Lin |
| 2012/0316606 A1 | 12/2012 | Farin |
| 2012/0330425 A1 | 12/2012 | Zipnick |
| 2013/0006313 A1 | 1/2013 | Binder |
| 2013/0023939 A1 | 1/2013 | Pischl |
| 2013/0023992 A1 | 1/2013 | Moskowitz |
| 2013/0046348 A1 | 2/2013 | Black |
| 2013/0053894 A1 | 2/2013 | Gamache |
| 2013/0053967 A1 | 2/2013 | Sournac |
| 2013/0060336 A1 | 3/2013 | Hooper |
| 2013/0060337 A1 | 3/2013 | Petersheim |
| 2013/0073045 A1 | 3/2013 | Vestgaarden |
| 2013/0131685 A1 | 5/2013 | Perrow |
| 2013/0138217 A1 | 5/2013 | Laurence |
| 2013/0150969 A1 | 6/2013 | Zipnick |
| 2013/0184749 A1 | 7/2013 | Lore |
| 2013/0197588 A1 | 8/2013 | Abdou |
| 2013/0197648 A1 | 8/2013 | Boehm |
| 2013/0204372 A1 | 8/2013 | Mohar |
| 2013/0245688 A1 | 9/2013 | Biedermann |
| 2013/0245765 A1 | 9/2013 | Lowry |
| 2013/0268008 A1 | 10/2013 | McDonough |
| 2013/0274813 A1 | 10/2013 | Mathieu |
| 2013/0282065 A1 | 10/2013 | Gorhan |
| 2013/0296941 A1 | 11/2013 | Perrow |
| 2013/0304124 A1 | 11/2013 | Dube |
| 2013/0304132 A1 | 11/2013 | Heilman |
| 2013/0310881 A1 | 11/2013 | Klein |
| 2013/0310937 A1 | 11/2013 | Pimenta |
| 2013/0317618 A1 | 11/2013 | Gause |
| 2013/0325074 A1 | 12/2013 | Ziolo |
| 2013/0345760 A1 | 12/2013 | Lombardo |
| 2014/0012329 A1 | 1/2014 | Kirschman |
| 2014/0039554 A1 | 2/2014 | Kim |
| 2014/0046377 A1 | 2/2014 | Hansell |
| 2014/0128924 A1 | 5/2014 | Perrow |
| 2014/0142641 A1 | 5/2014 | Black |
| 2014/0148905 A1 | 5/2014 | Messerli |
| 2014/0156009 A1 | 6/2014 | Armstrong |
| 2014/0163684 A1 | 6/2014 | Donner |
| 2014/0180417 A1 | 6/2014 | Bergey |
| 2014/0188177 A1 | 7/2014 | Jacene |
| 2014/0222085 A1 | 8/2014 | Black |
| 2014/0228892 A1 | 8/2014 | Cummins |
| 2014/0243908 A1 | 8/2014 | Konieczynski |
| 2014/0243909 A1 | 8/2014 | Campbell |
| 2014/0243985 A1 | 8/2014 | Lechmann |
| 2014/0277495 A1 | 9/2014 | Muhanna |
| 2014/0309704 A1 | 10/2014 | Hawkes |
| 2014/0324173 A1 | 10/2014 | Kirschman |
| 2014/0330386 A1 | 11/2014 | Walkenhorst |
| 2014/0336768 A1 | 11/2014 | Blain |
| 2014/0336771 A1 | 11/2014 | Zambiasi |
| 2014/0350682 A1 | 11/2014 | Bagga |
| 2015/0026958 A1 | 1/2015 | Doran |
| 2015/0032115 A1 | 1/2015 | LaPosta |
| 2015/0045840 A1 | 2/2015 | Vaucher |
| 2015/0051704 A1 | 2/2015 | Duffield |
| 2015/0066096 A1 | 3/2015 | Bush |
| 2015/0081027 A1 | 3/2015 | Thalgott |
| 2015/0088206 A1 | 3/2015 | Bullard |
| 2015/0094764 A1 | 4/2015 | Konieczynski |
| 2015/0100127 A1 | 4/2015 | Bal |
| 2015/0105824 A1 | 4/2015 | Moskowitz |
| 2015/0112395 A1 | 4/2015 | Day |
| 2015/0119992 A1 | 4/2015 | Kirschman |

FOREIGN PATENT DOCUMENTS

| | | |
|---|---|---|
| CN | 1366866 A | 9/2002 |
| CN | 201216642 Y | 4/2009 |
| CN | 202477905 A | 10/2012 |
| CN | 102860888 A | 1/2013 |
| CN | 102973336 A | 3/2013 |
| CN | 103099662 A | 5/2013 |
| CN | 202960832 A | 6/2013 |
| DE | 202008005076 | 9/2008 |

(56) References Cited

FOREIGN PATENT DOCUMENTS

| | | |
|---|---|---|
| DE | 202012006162 U1 | 9/2012 |
| EP | 0903113 A | 3/1999 |
| EP | 2340776 A | 1/2013 |
| FR | 2790198 A1 | 9/2000 |
| FR | 2874316 A | 2/2006 |
| FR | 2973221 A1 | 10/2012 |
| IN | 0328MUM2012 | 10/2009 |
| IN | 0784MUM2008 | 10/2009 |
| IN | 2981CHEN2011 A | 6/2013 |
| IN | 1327MUM2012 A | 12/2013 |
| IN | 1325MUM2012 | 5/2014 |
| JP | 2013075120 A | 4/2013 |
| KR | 20050032371 A | 4/2005 |
| WO | WO-0064359 | 11/2000 |
| WO | WO-0078238 | 12/2000 |
| WO | WO-2004017837 | 3/2004 |
| WO | WO-2004112627 | 12/2004 |
| WO | WO-2005053550 | 6/2005 |
| WO | WO-2006022644 | 3/2006 |
| WO | WO-2007037774 | 4/2007 |
| WO | WO-2010028095 | 3/2010 |
| WO | WO-2011012782 | 2/2011 |
| WO | WO-2011028236 | 3/2011 |
| WO | WO-2011092399 | 8/2011 |
| WO | WO-2012115631 | 8/2012 |
| WO | WO-2012141715 | 10/2012 |
| WO | WO-2012148499 | 11/2012 |
| WO | WO-2012148500 | 11/2012 |
| WO | WO-2013014590 | 1/2013 |
| WO | WO-2013048000 | 4/2013 |

\* cited by examiner

SPINAL FUSION IMPLANT AND RELATED METHODS

CROSS REFERENCE TO RELATED APPLICATIONS

This application is a continuation of commonly owned and co-pending U.S. patent application Ser. No. 13/361,855 (now U.S. Pat. No. 8,940,030), filed on Jan. 30, 2012, entitled "Spinal Fixation System and Related Methods", which claims the benefit of priority from U.S. Provisional Application Ser. No. 61/437,006, filed on Jan. 28, 2011, the entire contents of each are hereby expressly incorporated by reference into this disclosure as if set forth fully herein.

FIELD

The present invention relates generally to spinal surgery and, more particularly, to devices for spinal fixation and spinal fusion having an improved mechanism to prevent the back out of screws.

BACKGROUND

Currently there are nearly 500,000 spine lumbar and cervical fusion procedures are performed each year in the United States. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space. Anterior lumbar interbody fusion (ALIF) procedures provide unparalleled access to a desired spinal target site. The ALIF technique involves approaching the spine through the abdomen and exposing the front of the spine, as opposed to the side or the back. Approaching the spine this way generally allows for greater exposure and a more complete excision of the damaged disc. Introducing the intervertebral implant serves to restore the height between adjacent vertebrae ("disc height"), which reduces if not eliminates neural impingement commonly associated with a damaged or diseased disc.

SUMMARY

According to one embodiment, a surgical fixation system is described including a plate dimensioned to span at least two bony segments, a plurality of apertures dimensioned to receive anchor elements, a plurality of anchor elements and plurality anti-backout elements disposed adjacent to each of the apertures dimensioned to receive anchor elements.

According to an exemplary embodiment, the anti-backout element comprises a biasing member and a locking slide. The biasing member is elastically deformable. In a first position, the biasing member urges the locking slide in a first direction in which at least a portion of the locking slide enters the aperture in the plate. Upon insertion of an anchor element, the anchor element may force the locking slide to move in a second direction opposite the first direction, deforming the biasing member and moving the biasing member to a second position such that the locking slide does not reside in the aperture of the plate. Once the anchor element is fully inserted through the plate and passed the locking slide, the biasing member urges the locking slide in the first direction into the aperture such that at least a portion of the locking slide covers the proximal end of the anchor element preventing the anchor element from backing out of the plate.

According to another embodiment, a spinal fusion implant assembly is described. The spinal fusion implant assembly includes a plate coupled to a U-shaped body, a plurality of apertures in the plate dimensioned to receive anchor elements, a plurality of anchor elements and a plurality of anti-backout elements.

The anti-backout element includes a biasing member and locking slide and operates in the same way as described above for the surgical fixation system.

According to an exemplary aspect, the plate and the U-shaped body of the spinal fusion implant assembly are constructed of different materials. When fully assembled, the spinal fusion implant assembly is dimensioned to be contained entirely within an intervertebral disc space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
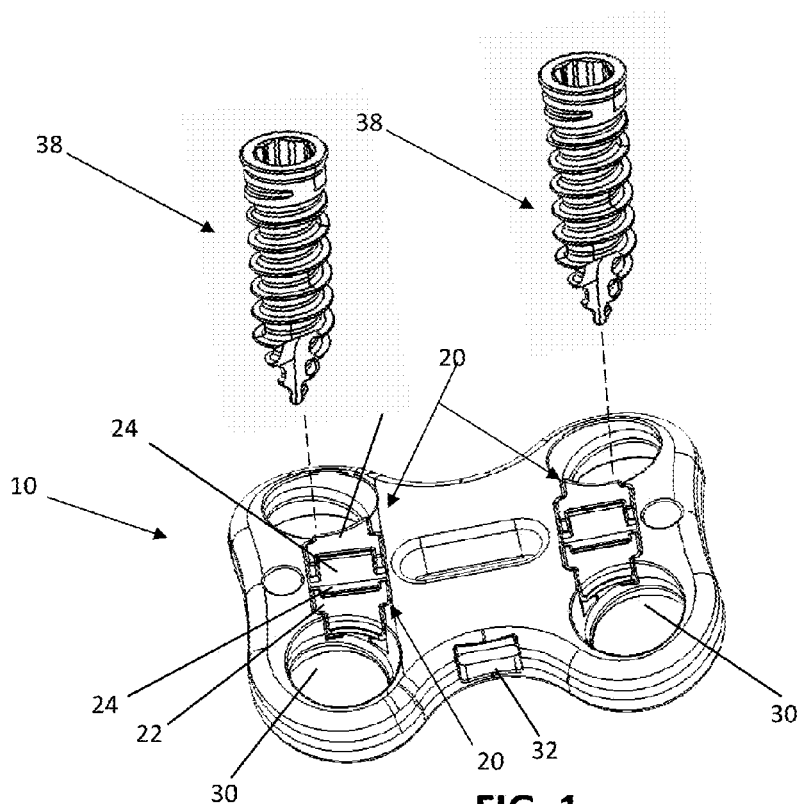
FIG. 1 is a perspective view of a spinal fixation system, according to an exemplary embodiment.
Figure 2:
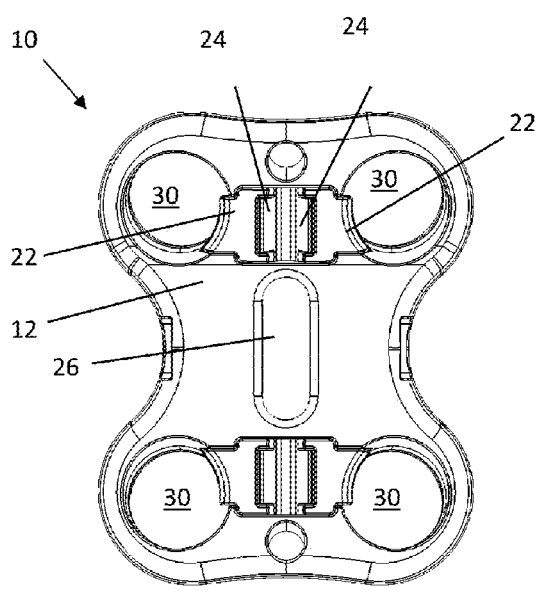
FIG. 2 is a top view of the spinal fixation plate of FIG. 1.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The spinal implants disclosed herein boast a variety of inventive features and components that warrant patent protection, both individually and in combination.

FIGS. 1-6 illustrate an example of a surgical fixation system, according to an exemplary embodiment. The surgical fixation system comprises a surgical fixation plate 10, a plurality of screws 38 (only two of four shown), and a plurality of anti-backout elements 20. As will be explained in greater detail below, the surgical fixation system may be used to provide temporary or permanent fixation along an orthopedic target site, including but not limited to adjacent vertebral levels within the spine (e.g. cervical spine during anterior fusion surgery, lumbar spine for anterior fusion surgery, etc. . . . ). To do so, the plate 10 is first positioned over the target site such that the screws and anti-backout elements 20 may thereafter be employed to couple the plate 10 to the target site. According to one aspect of the present invention, the screws 38 are prevented from backing out of the target site after placement through the use of the anti-backout elements 20 installed within the plate 10.

The surgical fixation plate 10 includes a first surface 12, a second surface 14, and a plurality of bone screw apertures 30 extending between the first and second surfaces 12, 14. Each bone screw aperture 30 has a corresponding anti-backout element 20 for preventing back-out of only one screw 38. The anti-backout element 20 resides in a recess 40 in first surface 12 of the plate 10 adjacent to the bone screw aperture 30.

The plate 10 may be provided having any number of different peripheral profiles, including but not limited to the generally rectangular peripheral profile set forth by way of example in the figures. The plate 10 may also be provided with or without a viewing aperture 40 formed between the first and second surfaces 12, 14 and positioned generally in the central portion of plate 10. The viewing aperture 40 functions to provide the ability to see or visualize the spinal target site after the plate 10 has been secured to the patient's vertebrae. It will be appreciated that the viewing aperture 40 may be provided in any number of suitable shapes or configurations without departing from the scope of the invention. Insertion tool recesses 32 may be provided on the lateral sides of the plate 10 for receiving at least a portion of an insertion instrument. By way of example only, the plate 10 shown in FIGS. 1-6 includes a pair of insertion tool recesses 32, with one located at each side of the plate 10.

Figure 3:
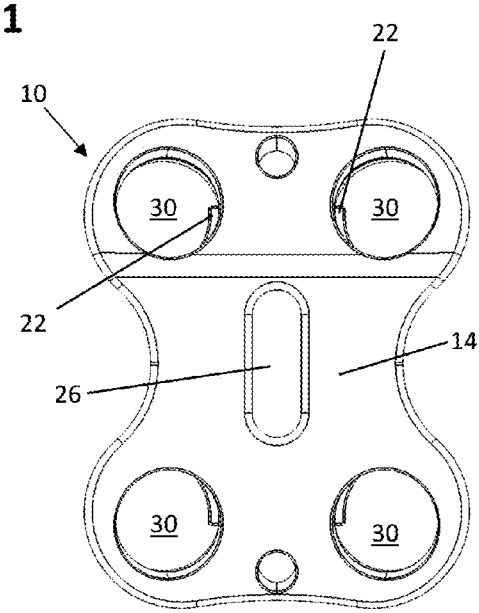
FIG. 3 is a bottom view of the spinal fixation plate of FIG. 1.
Figure 4:
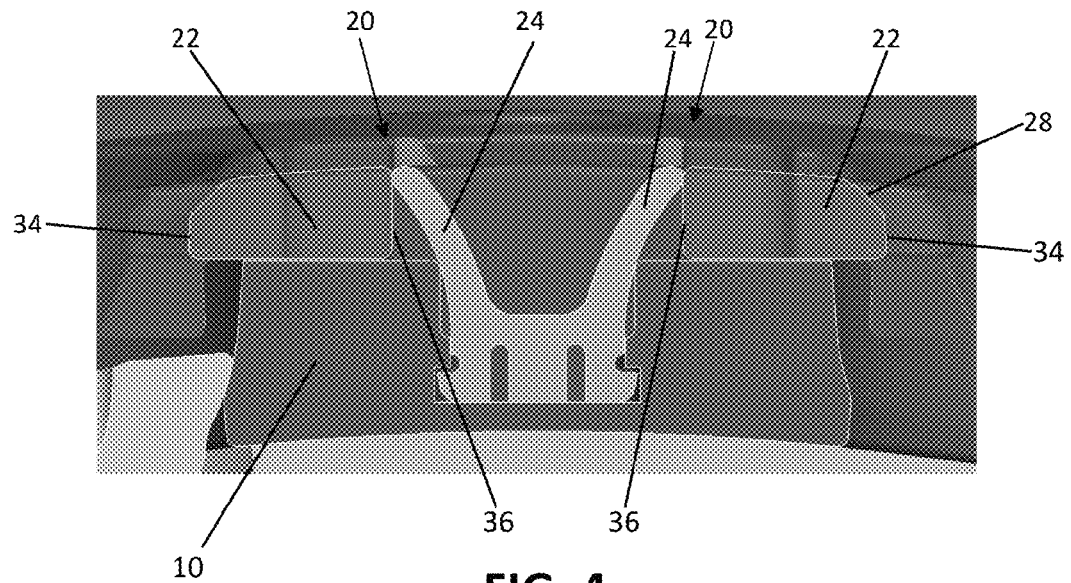
FIG. 4 is a cross-section of the width of the spinal fixation plate of FIG. 1.

FIGS. 1-6 illustrate a plate 10 having an anti-backout element 20 according to an exemplary embodiment. The anti-backout element 20 includes a locking slide 22 and a biasing member 24. The biasing member 24 is coupled to the plate 10 medial to the locking slide 22, and urges the locking slide 22 toward the screw aperture 30. The biasing member 24 is elastically deformable, such that when a bone screw 38 is inserted into the screw aperture 30, the head of the screw will urge the locking slide 22 away from the screw aperture 30 against the biasing member 24, thereby deforming the biasing member 24. Upon passage of the screw head past the locking slide 22, into the screw aperture 30, the biasing member 24 will urge the locking slide 22 back toward the screw aperture 30. At least a portion of the locking slide 22 will project into the screw aperture 30 (as best shown in FIG. 3), and over the proximal edge of the screw head, thereby preventing the screw from backing out of the screw aperture 30 of the plate 10 after insertion.

Figure 5:
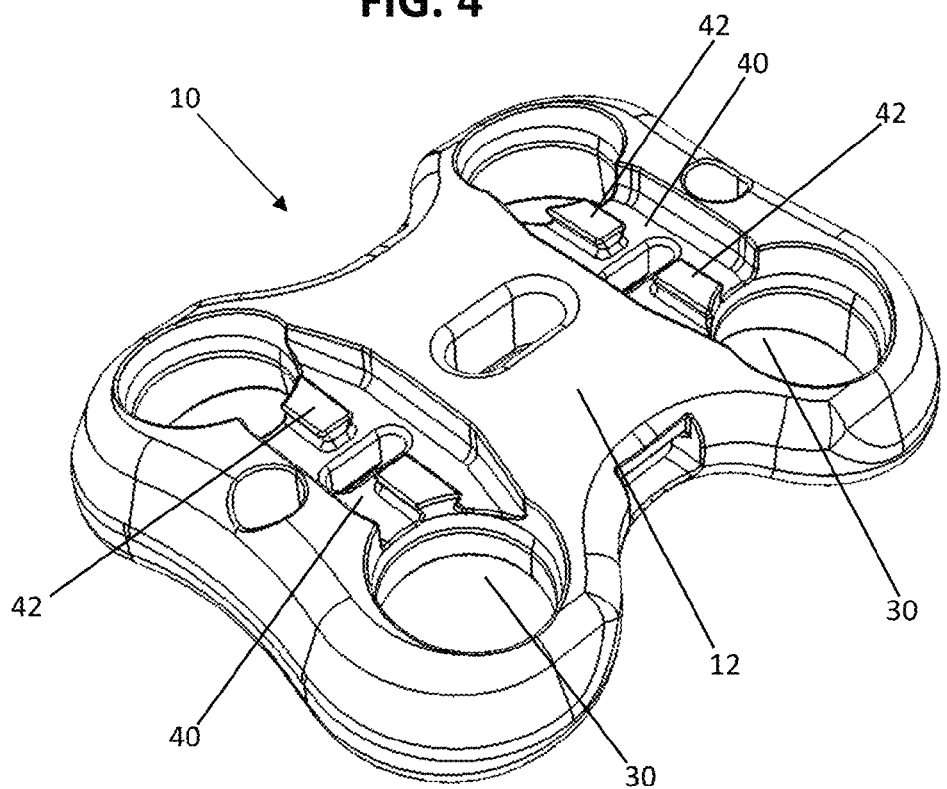
FIG. 5 is a perspective view of the spinal fixation plate of FIG. 1, without the anti-back-out mechanism.
Figure 6:
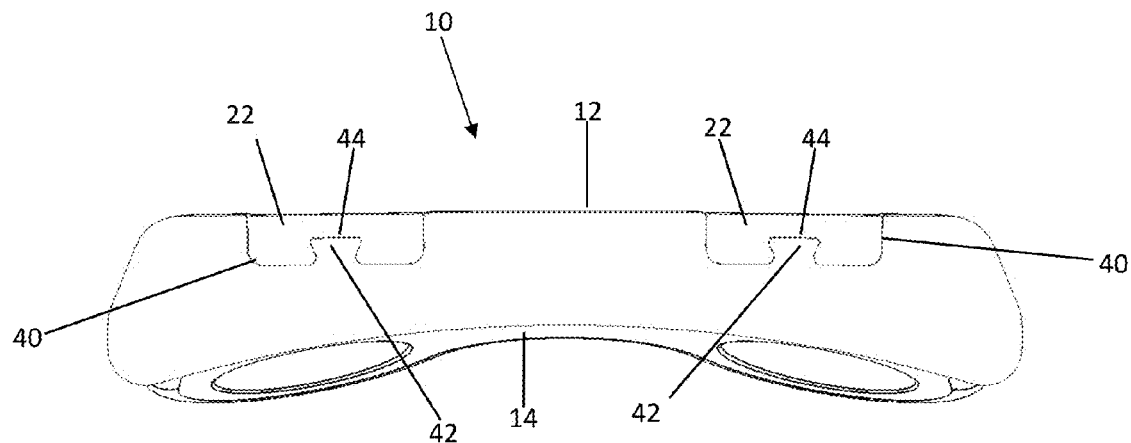
FIG. 6 is a cross-section along the longitudinal axis of the spinal fixation plate of FIG. 1.

The locking slide 22 has a medial face 36 for engaging the biasing member 24 and a lateral face 34 for engaging the head of a bone screw 38. According to the exemplary embodiment shown in FIGS. 1-6, the lateral face 34 that engages the head of a bone screw has a chamfered surface 28, such that during insertion of a bone screw 38 into a bone screw aperture 30 of the plate 10, when the head of the bone screw contacts the chamfered surface 28 of the locking slide 22, the medial surface 36 of the locking slide 22 will be urged against the biasing member 24 as discussed above. The locking slides may engage with the spinal fixation plate 10 within a recess 40 in the spinal fixation plate 10, wherein said recess 40 is located medially to a pair of screw apertures 30 (as best shown in FIG. 5). According to an exemplary embodiment, the locking slides 22 have a recess 44 that corresponds to a track 42 in the recess 40 in superior surface 12 of the plate 10. The track 42 engages the locking slide 22 via the recess 44 in the locking slide 22 and maintains the locking slide 22 within the plate 10. As such, the locking slide 22 is capable of sliding in a first direction toward its corresponding screw aperture 30 and in second direction, opposite the first direction, away from a corresponding screw aperture 30 and toward the biasing member 24.

Figure 7:
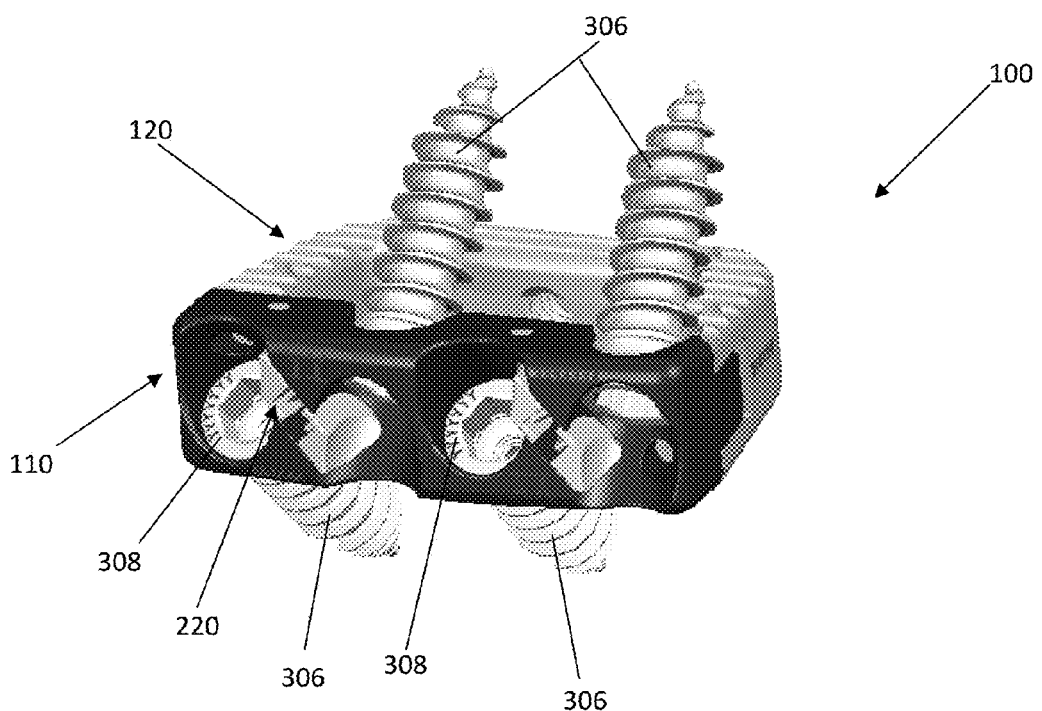
FIG. 7 is a perspective view of a spinal fusion implant assembly according to an exemplary embodiment.
Figure 8:
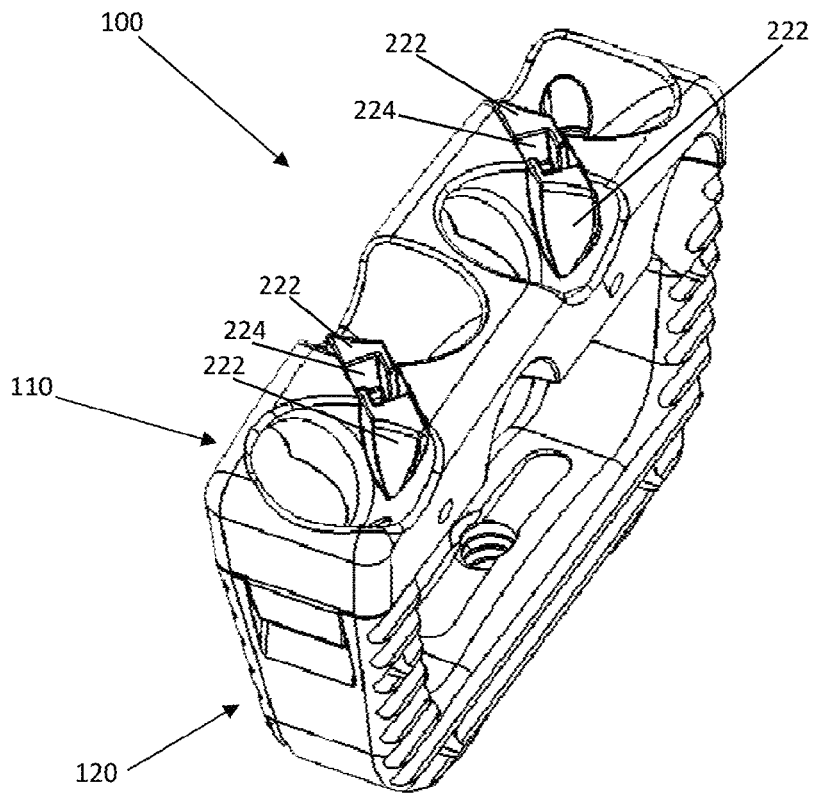
FIG. 8 is a perspective view of the spinal fusion implant assembly of FIG. 7.
Figure 12:
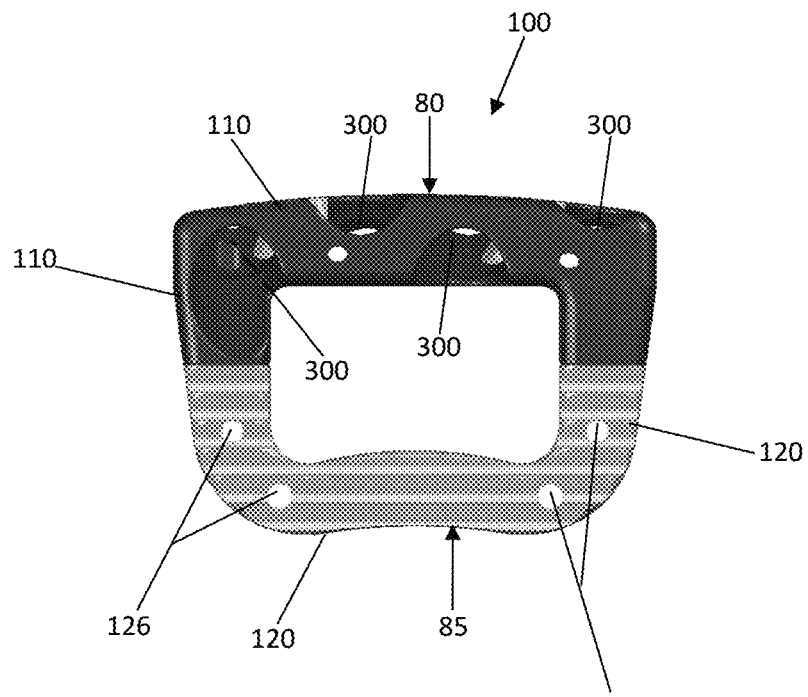
FIG. 12 is a top view of the spinal fusion implant assembly of FIG. 10.
Figure 13:
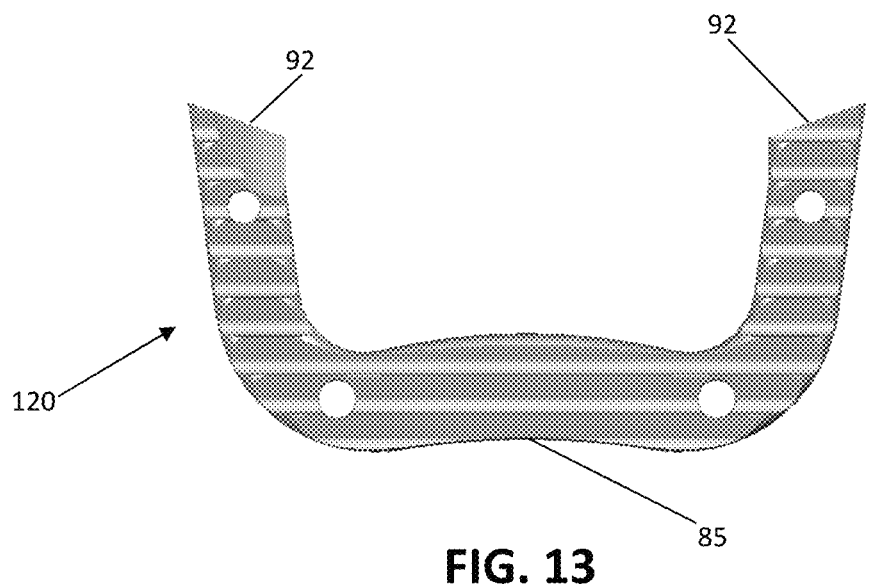
FIG. 13 is a front view of an alternative embodiment of the body of the implant assembly of FIGS. 7-12.

FIGS. 7-8 illustrate a spinal fusion implant assembly 100 according to an exemplary embodiment. The spinal fusion implant assembly 100 is a two-piece assembly including a plate 110 having locking elements 220, a plurality of bone screws 306 and a generally U-shaped body 120. The assembled two-piece implant 100 is dimensioned to be contained entirely within the intervertebral space when implanted. According to the exemplary embodiments, the plate 110 and body 120 are constructed of different materials. For example, the plate 110 may be constructed of any biocompatible metal, such as titanium. The body 120 may be constructed of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. According to an exemplary embodiment shown if FIG. 12, the arms of the U-shaped body may have chamfered surfaces where the body 120 engages the plate.

The spinal fusion implant assembly 100 includes a top surface 90, a bottom surface 95, two lateral sides, an anterior side 80, and a posterior side 85 (each defined relative to the regions of the target disc space when implanted). According to a preferred method of implantation the spinal fusion implant 100 may be implanted from an anterior approach such that anterior side 80 is the trailing side and posterior side 85 is the leading side during insertion. The plate 110 defines the anterior side 80 of the implant and includes a plurality of bone screw apertures 302, 304 each for receiving a bone screw therethrough. According to the exemplary embodiments, the screw apertures 302, 304 are positioned such that there is a lateral upper screw hole, a medial upper screw aperture, a lateral lower screw aperture, and a medial lower screw aperture.

The upper screw apertures 302 pass through the plate 110 at an angle such that when the bone screws 306 are inserted into the upper screw apertures 302, they extend from the plate 110 at an angle and penetrate into the vertebral body inferior to the implant assembly 100. By way of example only, the upper screw apertures 302 may be angled such that the bone screws penetrate into the vertebral body at an angle between 35 and 55 degrees, and preferably 45 degrees. Lower screw apertures 304 also pass through the plate 110 at an angle, but in the opposite direction of the upper screw apertures 302. Thus, when the bone screw 306 is inserted into the lower screw apertures 304, it extends from the plate 110 at an angle and penetrates the vertebral body superior to the implant assembly 100. By way of example, the lower screw apertures 304 may be angled such that the lower bone screws 306 penetrate into the vertebral body at an angle between 35 and 55 degrees, and preferably 45 degrees. The screw apertures 302, 304 may also be angled such that the distal end of the bone screws 306 converge towards each other. By way of example, the screw apertures 302, 304 may be oriented such that the bone screws 306 are angled medially between 5 and 15 degrees.

According to the exemplary embodiment illustrated in FIGS. 7-8, the plate 110 further includes an anti-backout element 220 that corresponds to each individual screw aperture 300. The anti-backout element 220 includes a locking slide 222 and a biasing member 224. The anti-backout element 220 functions in a way that is similar to the anti-backout element 20 described with respect to the spinal fixation plate 10 discussed above. A pair of locking elements 220 resides in a recess in the anterior surface of the plate 110 between a pair of screw apertures 300. The biasing member 224 is elastically deformable, such that when a bone screw 306 is inserted into the screw aperture 300, the head 308 of the screw will urge the locking slide 222 away from the screw aperture 300 against the biasing member 224, thereby deforming the biasing member 224. Upon passage of the screw head 308 past the locking slide 222, into the screw aperture 30, the biasing member 224 will urge the locking slide 222 back toward the screw aperture 300. At least a portion of the locking slide 222 will project into the screw aperture 300, and over proximal end of the screw head 308, thereby preventing the screw 306 from backing out of the screw aperture 300 of the plate 110 after insertion.

According to one embodiment, the body 120 includes at least one radiopaque marker 126. Further, the body 120 may also include anti-migration elements. Anti-migration features are designed to increase the friction between the spinal fusion implant assembly 100 and the adjacent contacting surfaces of the vertebral bodies so as to further prohibit migration of the spinal fusion implant 100 after placement and during the propagation of natural bony fusion. Such anti-migration features may include ridges (or teeth) provided along at least a portion of the top surface 90 and/or bottom surface 95.

Figure 9:
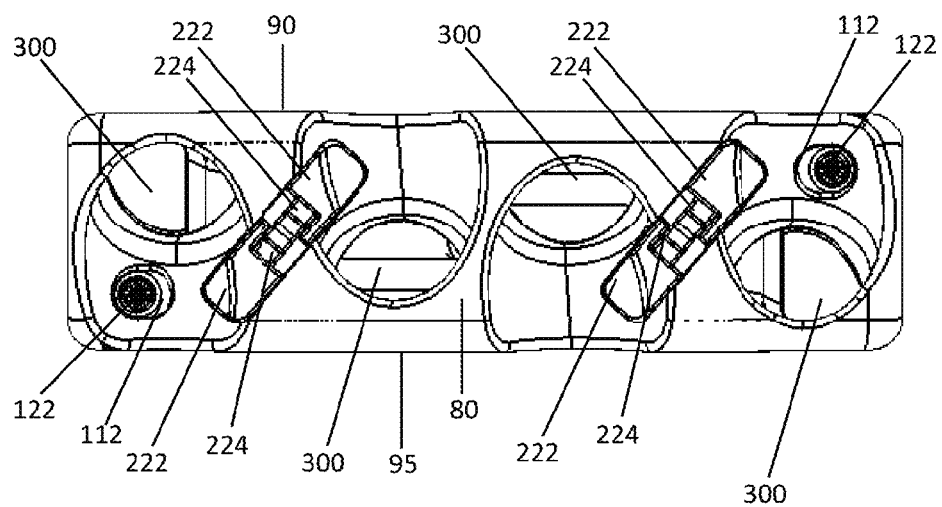
FIG. 9 is a front view of the spinal fusion implant assembly of FIG. 7.
Figure 10:
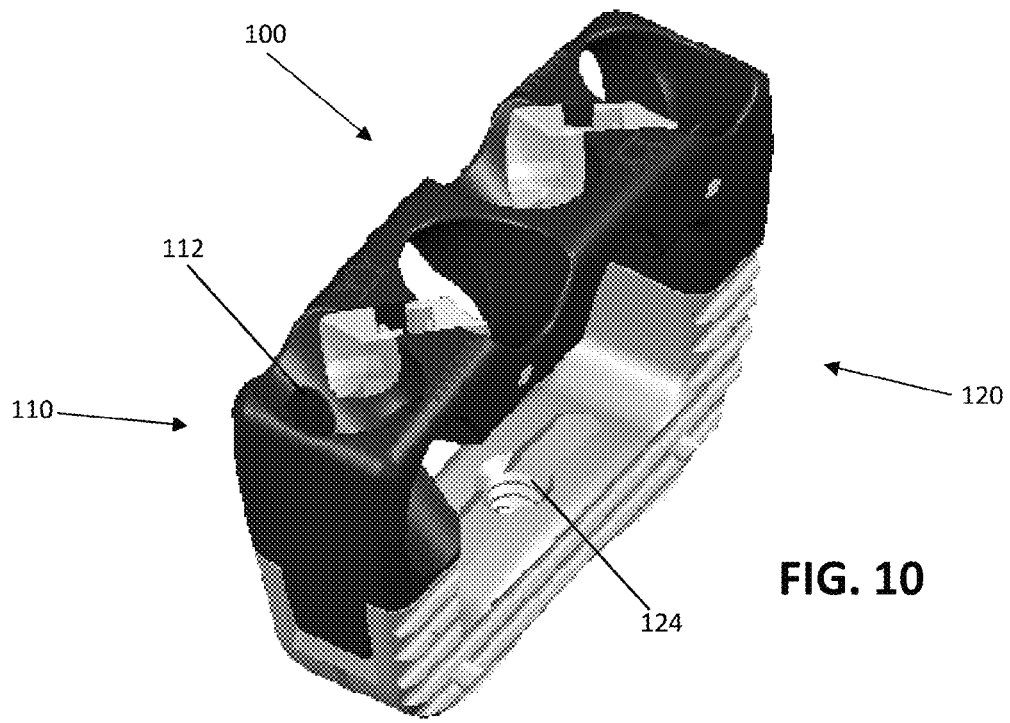
FIG. 10 is a perspective view of the spinal fusion implant assembly according to an alternate embodiment.
Figure 11:
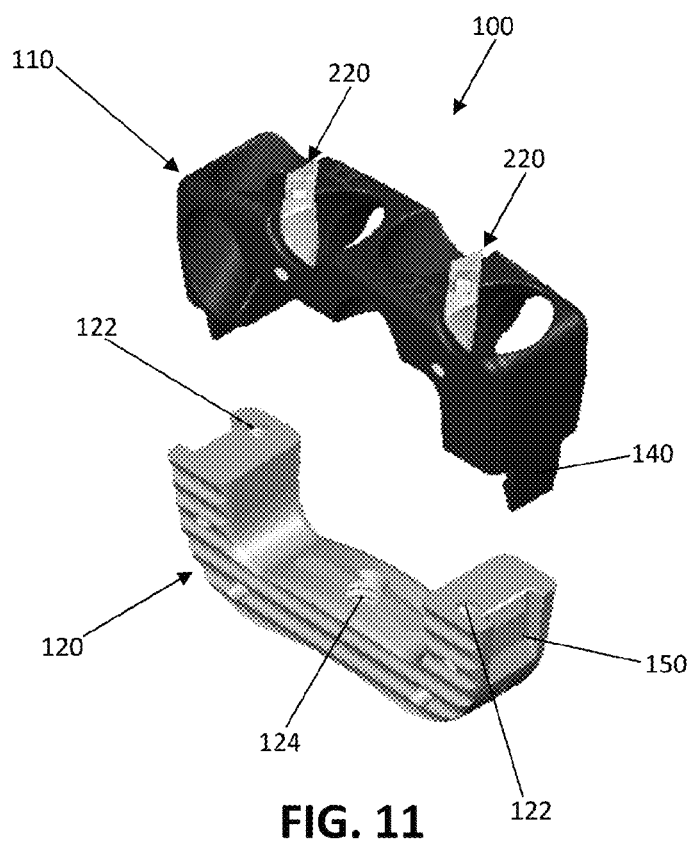
FIG. 11 is an exploded view of the spinal fusion implant assembly of FIG. 10.

FIGS. 9-11 illustrate an alternative embodiment of the spinal fusion implant assembly 100. This embodiment includes all of the same features as the exemplary embodiment of FIGS. 7-8. According to this embodiment, the plate 110 is generally U-shaped and the body 120 is generally U-shaped. The screw apertures 300 extend through the plate 110 from the anterior surface 80 through the top surface 90 (for lower screw apertures) of the plate 110 or the bottom surface 95 (for upper screw apertures) of the plate 110.

With regard to the embodiment shown in FIGS. 7-11, it is contemplated that the spinal fusion implant assembly 100 can be assembled prior to insertion into the intervertebral space and implanted as a single complete implant, or the implant assembly 100 can be assembled within the intervertebral disc space in a multi-step process including inserting the body 120 into the intervertebral space, packing the body 120 and/or disc space adjacent the body 120 with bone growth enhancing material, then inserting the plate 110 and coupling the plate 110 to the body 120, thereby enclosing bone growth material in the interior space of the implant assembly 100. Both methods of implantation are preferably achieved through a standard anterior approach. In order to facilitate assembly of the implant 100 within the intervertebral space, the body 120 includes an insertion tool aperture 124 to enable the body 120 of the assembly to be implanted in the intervertebral space before the plate 110.

According to the embodiments shown in FIGS. 7-11, the body further includes apertures 122 dimensioned to receive a guide element, such as a pin or wire (not shown). By way of example only, the guide element apertures 122 may be threaded to receive a guide element with a threaded distal end. Accordingly, the plate 110 also includes apertures 112 dimensioned to allow passage of a guide element therethough. The guide apertures 122 in the body align with the guide apertures 112 in the plate, such that after the body 120 is implanted in the intervertebral space with guide elements attached, the plate 110 can be inserted to align with the body 120. The plate 110 further includes engagement features 140 that correspond to engagement features 150 on the body to facilitate coupling of the plate 110 to the body 120 upon insertion of the plate 110 into the intervertebral space. Once the plate 110 is coupled to the body 120 within the disc space, the guide elements may be removed from the implant assembly 100.

The spinal fusion implant assembly 100 may be used to provide temporary or permanent fixation along an orthopedic target site. Once deposited in the intervertebral disc space, the spinal implant assembly 100 effects spinal fusion over time as the natural healing process integrates and binds the implant 100 within the intervertebral space by allowing a bony bridge to form through the implant 100 and between the adjacent vertebral bodies. Top surface 90 and opposed bottom surface 90 are both adapted for contact with the upper and lower vertebra adjacent the disc space. Bone screws may be introduced through the screw apertures 300 and into the adjacent vertebral bodies to fix the implant assembly 100 in the desired position within the disc space.

According to an additional embodiment, the top and bottom surfaces 90, 95 may be angled between the anterior side 80 and posterior side 85. In lumbar and cervical applications, the posterior side 85 will preferably be shorter in height than the anterior side 80 such that the implant 100 tapers down from anterior side 80 to posterior side 85. For example, the posterior-to-anterior angle of the tapered top and bottom surfaces 80, 85 may range from 5° and 15° relative to a horizontal axis, and preferably 8° to 12°. In this manner, the implant 100 helps maintain the adjacent vertebral bodies in lordosis, which is the natural curvature found in the lumbar and cervical regions of the spine. The top and bottom surfaces 80, 85 may be configured in any number of suitable shapes to better match the natural contours of the vertebral end plates, such as, for example, concave, convex, or a combination of concave and convex.

Fusion may be facilitated or augmented by introducing or positioning various osteoinductive materials within cavity between the plate 110 and the body 120 and/or adjacent to the spinal fusion implant assembly 100 within the intervertebral space. Such osteoinductive materials may be introduced before, during, or after insertion of the exemplary spinal fusion implant assembly 100, and may include (but are not necessarily limited to) autologous bone harvested from the patient receiving the spinal fusion implant assembly 100, bone allograft, bone xenograft, any number of non-bone implants (e.g. ceramic, metallic, polymer), bone morphogenic protein, and bio-resorbable compositions, including but not limited to, any of a variety of poly (D, L-lactice-co-glycolide) based polymers.

What is claimed is:

1. A spinal fusion implant for insertion between first and second vertebral bodies, said spinal fusion implant comprising:

a body having a top surface and an opposing bottom surface, opposing first and second lateral sides, a posterior wall and an anterior wall, wherein the anterior wall includes a plurality of apertures, each of the plurality of apertures configured to receive an anchor element therethrough;

a plurality of anchor elements configured to anchor the body to at least one of the first and second vertebral bodies, each of the anchor elements dimensioned to be received through one of the plurality of apertures; and a plurality of anti-backout elements disposed adjacent to each of the plurality of apertures, such that one anti-backout element is associated with one aperture, the anti-backout elements comprising a locking slide, which includes a concave portion with concavity toward the center of the aperture, and a biasing member, wherein the biasing member is physically distinct from the locking slide and elastically deformable from a first position urging said concave portion of said locking slide in a first direction into the aperture to a second position wherein said locking slide urges said biasing member in a direction opposite said first direction.

2. The spinal fusion implant of claim 1, wherein the locking slide is configured such that when the anchor element is inserted into the aperture, a head of the anchor element will move the locking slide away from the aperture and against the biasing member.

3. The spinal fusion implant of claim 2, wherein the biasing member and locking slide are configured such that when the anchor element is fully inserted within the aperture, the biasing member will push the locking slide at least partially into the aperture.

4. The spinal fusion implant of claim 3, wherein a portion of the locking slide projects into the aperture, and over a proximal end of the anchor element head, thereby preventing the anchor from backing out of the aperture of the spinal plate after insertion.

5. The spinal fusion implant of claim 1, wherein the anti-backout element resides in a recess in an anterior surface of the anterior wall.

6. The spinal fusion implant of claim 5, wherein the anti-backout element is positioned between a pair of apertures.

7. The spinal fusion implant of claim 1, further comprising a radiopaque marker.

8. The spinal fusion implant of claim 1, wherein the top and bottom surfaces include anti-migration features to increase friction with adjacent contacting surfaces.

9. The spinal fusion implant of claim 8, wherein the anti-migration features include ridges.

10. The spinal fusion implant of claim 1, wherein the anterior wall is detachable from the body.

11. The spinal fusion implant of claim 10, wherein the anterior wall is composed of titanium.

12. The spinal fusion implant of claim 1, wherein the plurality of apertures are angled so that the anchor elements enter the anterior wall at two different angles.

13. The spinal fusion implant of claim 12, wherein each angle is between 35 and 55 degrees.

14. The spinal fusion implant of claim 13, wherein each angle is 45 degrees.

15. The spinal fusion implant of claim 1, wherein the plurality of apertures comprise four apertures, including two pairs, each pair comprising apertures which position the anchor elements at equal angles.

16. The spinal fusion implant of claim 15, wherein the apertures are positioned so that the shafts of the anchor elements diverge upon insertion through the apertures.

17. The spinal fusion implant of claim 16, wherein at least one pair of apertures is configured to direct the anchor elements into the first vertebral body.

18. The spinal fusion implant of claim 17, wherein one pair of apertures is configured to direct the anchor elements into the second vertebral body.

19. The spinal fusion implant of claim 1, wherein in the second position, said concave portion of said locking slide is substantially linear with an outer perimeter of said aperture.

20. The spinal fusion implant of claim 1, wherein said locking slide further comprises a pointed tip portion extending further centrally and inward with respect to said aperture than said concave portion of said locking slide.

* * * * *